(12) United States Patent
Brubaker et al.

(10) Patent No.: US 8,222,272 B2
(45) Date of Patent: Jul. 17, 2012

(54) PHARMACEUTICAL FORMULATION AND PROCESS COMPRISING A SOLID DISPERSION OF MACROLIDE (TACROLIMUS)

(75) Inventors: Greg A. Brubaker, Sunbury, OH (US); Thomas D. Mahon, West Jefferson, OH (US)

(73) Assignee: Roxane Laboratories, Inc., Columbus, OH (US)

( * ) Notice: Subject to any disclaimer, the term of this patent is extended or adjusted under 35 U.S.C. 154(b) by 174 days.

(21) Appl. No.: 12/101,500

(22) Filed: Apr. 11, 2008

(65) Prior Publication Data

US 2009/0258895 A1    Oct. 15, 2009

(51) Int. Cl.
*A61K 31/436*    (2006.01)
*A61P 37/06*    (2006.01)

(52) U.S. Cl. ........................................ 514/294
(58) Field of Classification Search .................. 514/294
See application file for complete search history.

(56) References Cited

U.S. PATENT DOCUMENTS

| | | |
|---|---|---|
| 4,916,138 A | 4/1990 | Ueda et al. |
| 5,601,844 A | 2/1997 | Kagayama et al. |
| 6,316,473 B1 | 11/2001 | Shimojo et al. |
| 6,346,537 B1 | 2/2002 | Hata et al. |
| 6,440,458 B1 | 8/2002 | Yamashita et al. |
| 6,576,259 B2 | 6/2003 | Yamashita et al. |
| 6,884,433 B2 | 4/2005 | Yamashita et al. |
| 2003/0215496 A1 | 11/2003 | Patel et al. |
| 2004/0018228 A1 | 1/2004 | Fischell et al. |
| 2006/0287352 A1* | 12/2006 | Holm et al. .................... 514/291 |

OTHER PUBLICATIONS

Prograf(r) Summary Basis of Approval, NDA 50-708 and 50-709, Biopharmaceutics Review, pp. 7-11 (1994).
Prograf(r) Summary Basis of Approval, NDA 5-708 and 50-709, Biopharmaceutics Review Section, p. 1 (1994).
Chemistry Review #1 NDA 50-708, p. 3 (1994).
Kazunari Yamashita et al., "Establishment of new preparation method for solid dispersion formulation of tacrolimus," International Journal of Pharmaceuticas, 267, 2003, 79-91.
Sarfaraz K. Niazi, "Uncompressed Solids Formulations," Handbook of Pharmaceutical Manufacturing Formulations—Uncompressed Solid Products, vol. 2, p. 175, no date available, Apr. 27, 2004.

* cited by examiner

*Primary Examiner* — San-Ming Hui
*Assistant Examiner* — Kathrien Cruz
(74) *Attorney, Agent, or Firm* — Pearne & Gordon LLP

(57) ABSTRACT

The present invention relates to a pharmaceutical formulation and process for preparing the same comprising an oral dosage formulation, such as a capsule formulation, of a macrolide compound, such as tacrolimus, wherein the capsule formulation contains both a solid dispersion of the macrolide along with a non-dispersed form of the macrolide. The pharmaceutical formulation according to the invention is bioequivalent to the FDA approved product according to a bioavailability study conducted in humans.

15 Claims, No Drawings

PHARMACEUTICAL FORMULATION AND PROCESS COMPRISING A SOLID DISPERSION OF MACROLIDE (TACROLIMUS)

FIELD OF THE INVENTION

The present invention relates to a pharmaceutical formulation and process for preparing the same comprising an oral dosage formulation, such as a capsule, of a macrolide compound wherein the oral dosage formulation contains both a solid dispersion of the macrolide along with a non-dispersed form of the macrolide. The pharmaceutical formulation according to the invention is bioequivalent to the brand product according to bioavailability studies conducted in humans.

BACKGROUND OF THE INVENTION

Compounds of the formula (I), commonly known as "macrolides", are known in the art:

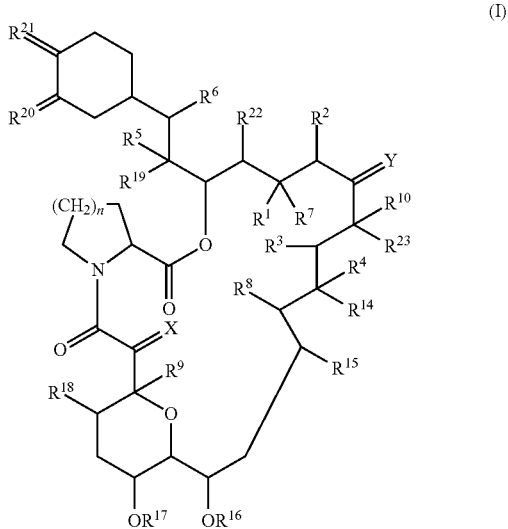

(I)

wherein each vicinal pair of $R^1$ and $R^2$, $R^3$ and $R^4$, $R^5$ and $R^6$ independently may,
  a) represent two vicinal hydrogen atoms, or
  b) form a second bond between the vicinal carbon atoms to which they are attached; in addition to the meanings above, $R^2$ may represent an alkyl group;

$R^7$ represents hydrogen, hydroxy group, protected hydroxy or alkyloxy group or, in conjunction with $R^1$, it may represent oxo group;

$R^8$ and $R^9$ independently represent hydrogen or hydroxy group; $R^{10}$ represents hydrogen, alkyl group, alkyl group substituted by one or more hydroxy groups, alkenyl group, alkenyl group substituted by one or more hydroxy groups, or alkyl group substituted by oxo group;

X represents oxo group, (hydrogen atom, hydroxy group), (hydrogen atom, hydrogen atom) or —$CH_2O$—;

Y represents oxo group, (hydrogen atom, hydroxy group), (hydrogen atom, hydrogen atom) or N—$NR^{11}R^{12}$ or N—$OR^{13}$;

$R^{11}$ and $R^{12}$ independently represent hydrogen atom, or alkyl, aryl or tosyl group;

$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;

$R^{20}$ and $R^{21}$ independently represent oxo group, or they may independently represent ($R^{20}_a$, hydrogen atom) and ($R^{21}_a$, hydrogen atom) respectively; $R^{20}_a$ and $R^{21}_a$ independently represent hydroxy group, alkyloxy group, or $OCH_2OCH_2CH_2OCH_3$ or $R^{21}_a$ is protected hydroxy group;

in addition $R^{20}_a$ and $R^{21}_a$ may together represent an oxygen atom in an epoxide ring;

n is 1, 2 or 3;

in addition to the meanings above, Y, $R^{10}$ and $R^{23}$, together with the carbon atoms to which they are attached, may represent a 5- or 6-membered N-, S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —$CH_2Se(C_6H_5)$.

The macrolide compounds represented by formula (I) are known to possess immunosuppressive activity when administered to patients in need thereof. One compound of particular interest is 17-allyl-1,14-dihydroxy-12-[2-(4-hydroxy-3-methoxy-cyclohexyl)-1-methylvinyl)-23,25-dimethoxy-13,19,21,27-tetramethyl-11,28-dioxa-4-azatricyclo[22.3. $1.0^{4,9}$]octacos-18-ene-2,3,10,16-tetraone, commonly referred to as tacrolimus or FR-900506 (FK506). Tacrolimus possesses immunosuppressive as well as antimicrobial activity and is therefore useful for the treatment and prevention of rejection of transplantation, graft-vs.-host diseases, auto-immune diseases, infectious diseases and the like.

Compounds according to formula (I), along with their pharmaceutically acceptable salts, are known in the art to be produced by fermentation of *Streptomyces tsukubaensis* No. 9993 (FERM BP-927) or *Streptomyces hygroscopicus* subsp. *yakushimaensis* No. 7238 (FERM BP-928).

Solid dispersions of macrolides, including tacrolimus, are known in the art. Yamashita et al (International Journal of Pharmaceutics, vol. 267, pp. 79-91, (2003)) describes a solid dispersion of tacrolimus in which the entire dosage amount of tacrolimus is formulated by dissolving the tacrolimus in ethanol, adding hydroxypropylmethyl cellulose (HPMC) as a carrier and evaporating the ethanol under vacuum at 40° C.

It is desirable to develop additional solid dispersion formulations of macrolide compounds, such as tacrolimus, which are bioequivalent to FDA approved formulations of those same compounds.

SUMMARY OF THE INVENTION

The present invention relates to a pharmaceutical formulation and process for preparing the same comprising an oral dosage formulation of a macrolide compound, such as tacrolimus, wherein the oral dosage formulation contains both a solid dispersion of the macrolide along with a non-dispersed form of the macrolide, such as a crystalline form, for example.

One aspect of the invention includes a pharmaceutical formulation comprising a pharmaceutically acceptable amount of a macrolide compound of the formula (I):

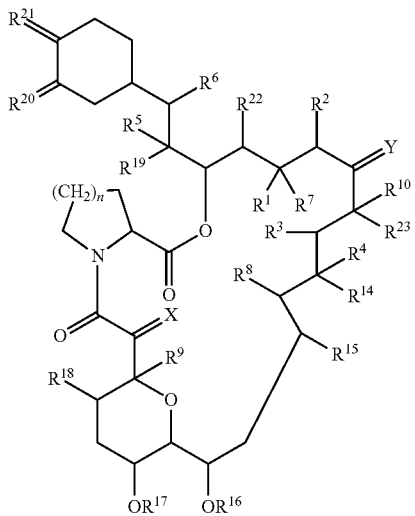

wherein each vicinal pair of $R^1$ and $R^2$, $R^3$ and $R^4$, $R^5$ and $R^6$ independently may,
a) represent two vicinal hydrogen atoms, or
b) form a second bond between the vicinal carbon atoms to which they are attached;
in addition to the meanings above, $R^2$ may represent an alkyl group;
$R^7$ represents hydrogen, hydroxy group, protected hydroxy or alkyloxy group or, in conjunction with $R^1$, it may represent oxo group;
$R^8$ and $R^9$ independently represent hydrogen or hydroxy group; $R^{10}$ represents hydrogen, alkyl group, alkyl group substituted by one or more hydroxy groups, alkenyl group, alkenyl group substituted by one or more hydroxy groups, or alkyl group substituted by oxo group;
X represents oxo group, (hydrogen atom, hydroxy group), (hydrogen atom, hydrogen atom) or —$CH_2O$—;
Y represents oxo group, (hydrogen atom, hydroxy group), (hydrogen atom, hydrogen atom) or N—$NR^{11}R^{12}$ or N—$OR^{13}$;
$R^{11}$ and $R^{12}$ independently represent hydrogen atom, or alkyl, aryl or tosyl group;
$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;
$R^{20}$ and $R^{21}$ independently represent oxo group, or they may independently represent ($R^{20}_a$, hydrogen atom) and ($R^{21}_a$, hydrogen atom) respectively; $R^{20}_a$ and $R^{21}_a$ independently represent hydroxy group, alkyloxy group, or $OCH_2OCH_2CH_2OCH_3$ or $R^{21}_a$ is protected hydroxy group;
in addition $R^{20}_a$ and $R^{21}_a$ may together represent an oxygen atom in an epoxide ring;
n is 1, 2 or 3;
in addition to the meanings above, Y, $R^{10}$ and $R^{23}$, together with the carbon atoms to which they are attached, may represent a 5- or 6-membered N-, S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —$CH_2Se(C_6H_5)$;
in an oral dosage form, wherein the oral dosage comprises a solid dispersion of the macrolide compound and a non-dispersed form of the macrolide compound, wherein the amount of macrolide compound in the solid dispersion is from about 50% to about 85% of total macrolide compound in the formulation and the remainder of the macrolide compound is non-dispersed, wherein the combined amount of macrolide compound in solid dispersion form and macrolide compound in non-dispersed form equals 100% of the pharmaceutically acceptable amount.

A further aspect of the invention relates to a process for preparing a pharmaceutical formulation comprising a pharmaceutically acceptable amount of a macrolide compound of the formula (I) as described above comprising the steps of:
a) dissolving from about 50% to about 85% of the total amount of macrolide compound to be used in the formulation in a solvent to form a macrolide solution;
b) mixing the macrolide solution of step (a) with one or more carriers;
c) drying the mixture on the carrier(s) to form a solid dispersion; further wherein the solid dispersion is then processed as follows:
d) milling the solid dispersion of step c) and the remainder of the total amount of macrolide compound, filler materials and/or disintegrants;
e) blending the milled materials of step d);
f) adding lubricants and blending to form a final blend;
g) processing the final blend into an oral dosage form.

An optional step of roller compaction may be included in the above process, typically after step (e).

An additional aspect of the invention relates to a pharmaceutical formulation comprising tacrolimus as the active ingredient, wherein a portion of the tacrolimus is present in a solid dispersion in an amount of from about 50% to about 85%, preferably from about 55% to about 75%, more preferably about 65%, of the total amount of tacrolimus in the formulation and the carrier for the solid dispersion is hydroxypropylmethyl cellulose (HPMC).

A further aspect of the invention relates to a pharmaceutical formulation comprising tacrolimus as the active ingredient, wherein a portion of the tacrolimus is present in a solid dispersion and the formulation is bioequivalent, within the meaning of FDA standards of bioequivalency, to the FDA approved product in bioavailability studies conducted in humans.

These and other aspects of the invention will be understood by those of ordinary skill in the art in view of the following detailed description and claims.

DETAILED DESCRIPTION OF THE INVENTION

In accordance with the present invention, a pharmaceutical formulation comprising a macrolide compound of formula (I) is provided where a portion of the macrolide compound is in a solid dispersion form and the remainder of the macrolide compound is in a non-dispersed form.

In particular, a macrolide compound of formula (I), such as tacrolimus, is provided in an oral dosage form, such as, for example, a capsule, in a pharmaceutically acceptable amount which provides immunosuppressive activity to a patient in need thereof. The macrolide compound is initially obtained in a non-dispersed form which is typically crystalline. It is then separated into two portions wherein one portion, containing from about 50% to about 85% of the total macrolide, is processed into a solid dispersion.

The process of the invention which is used to prepare the solid dispersion portion of the macrolide formulation involves the following steps:
a) dissolving from about 50% to about 85% of the total amount of macrolide compound to be used in the formulation in a solvent to form a macrolide solution;
b) mixing the macrolide solution of step (a) with a carrier;
c) drying the mixture on the carrier to form a solid dispersion.

This solid dispersion is then blended with the remaining non-dispersed form of the macrolide, and milled to size. Conventional formulation adjuvants, such as fillers, disintegrants and lubricants, are added to the formulation and the final formulation is then formed into the final oral dosage form, such as capsules. An optional step involving roller compaction of the milled product may be utilized as well. Typical capsules are formulated into dosages of 5.0 mg, 1.0 mg and 0.5 mg active ingredient strengths.

With respect to solvents useable in step (a) of the process, any type of solvent which dissolves the macrolide and which is essentially free of water will be appropriate. Alcohols (anhydrous and dehydrated), such as pure alcohols (200 proof), ethanol (anhydrous or dehydrated), denatured alcohol, propylene glycol, polyethylene glycols, and methanol can be used along with other solvents such as chloroform, acetone, dimethylformamide, ethyl ether, dichloromethane and trichloromethane. When tacrolimus is the macrolide, a preferred solvent is pure ethanol.

With respect to the carriers useable in accordance with the invention, any carrier or blend of carriers which accepts the dissolved drug/solvent mixture is acceptable. Carriers useable in accordance with the invention include, but are not limited to, hydroxypropylmethyl cellulose (HPMC, hypromellose), hydroxyethyl cellulose, hydroxyethylmethyl cellulose, hydroxypropyl cellulose, hypromellose phthalate, cellulose acetate, cellulose acetate phthalate, methylcellulose, ethylcellulose, cellulose, carboxymethylcellulose, microcrystalline cellulose, silicified microcrystalline cellulose, hydroxypropyl starch, polyethylene glycols, polyvinylpyrrolidone, polyglycolized glycerides, polymethacrylates, carrageenan, chitosans and starches (including corn, potato, rice, wheat, fully pregelatinized and partially gelatinized). When tacrolimus is the macrolide, a preferred carrier is HPMC, Methocel E5 (Premium) LV, which has a nominal viscosity of 5 mPas in a 2% w/v aqueous solution. Other grades of HPMC, such as those having nominal viscosities between 3 and 100,000 mPas in a 2% w/v aqueous solution, are also suitable.

Fillers which are useable in accordance with the invention include, but are not limited to, lactose (anhydrous), lactose monohydrate, spray-dried lactose; compressible sugar, dextrose, dextrates; starches (including corn, potato, rice, wheat, fully pregelatinized and partially gelatinized); inorganic salts such as calcium phosphate, tribasic calcium and calcium sulfate; and polyols such as mannitol, sorbitol and xylitol. When tacrolimus is used as the macrolide, a preferred filler is lactose, anhydrous.

Disintegrants which are useable in accordance with the invention include, but are not limited to, croscarmellose sodium, sodium starch glycolate, starches (including corn, potato, rice, wheat, fully pregelatinized and partially gelatinized), crospovidone, alginates such as calcium alginate and sodium alginate, alginic acid, and magnesium aluminum silicate. When tacrolimus is used as the macrolide, a preferred disintegrant is croscarmellose sodium.

Lubricants which are useable according to the invention include, but are not limited to, magnesium stearate, calcium stearate, zinc stearate, stearic acid, sodium stearyl fumarate, hydrogenated vegetable oils, mineral oil, polyethylene glycols, talc, glyceryl behenate, glyceryl monostearate, glyceryl palmitostearate, leucine, and magnesium lauryl sulfate. When tacrolimus is used as the macrolide, a preferred lubricant is magnesium stearate.

Pharmaceutical formulations produced according to the process of the present invention have been shown to be bioequivalent to FDA approved formulations. Specifically, a tacrolimus formulation comprising from 50-85% tacrolimus as a solid dispersion has been shown to be bioequivalent to the reference listed brand product as specified by the FDA Orange Book. More specifically, a tacrolimus formulation comprising 65% tacrolimus on an HPMC carrier and 35% non-dispersed tacrolimus has been shown to be bioequivalent to the reference listed brand product as specified by the FDA Orange Book wherein parameters, such as rate of absorption, $C_{max}$, and extent of absorption, Area Under the Curve (AUC), are nearly identical for fasted patients.

The following provides an example of a pharmaceutical formulation, comprising tacrolimus as the active ingredient, which is prepared in accordance with the process of the instant invention.

EXAMPLE

This example details the production of a 180,000 lot of 5.0 mg capsules of tacrolimus according to the invention.

To a stockpot, 1.290 kg of alcohol, USP (200 proof) was added with standard mixing. To the alcohol, 299 g of tacrolimus was added and dissolved with standard mixing. To a mixer, 1.350 kg of hypromellose, USP (Methocel E5 (Premium) LV), was added along with the tacrolimus/alcohol solution. The mixture was granulated for ten minutes and the granulated mixture scraped from the walls of the bowl and agitator. The mixture was then granulated for another ten minutes and discharged into a container. The above process was then repeated to generate a second, duplicate batch of granulated tacrolimus.

The two batches of granulated tacrolimus were then combined and passed through a #14 mesh screen and then dried at 140° F. to a moisture content of 0.30-1.50% thereby producing the solid dispersion portion of the capsule formulation.

Next, 720 g croscarmellose sodium, NF (AC-DI-SOL (Modified Cellulose Gum)), and 8.890 kg lactose, NF (anhydrous) were passed through a model 194 Quadro Comil and collected in container 1. Then, 900 g of lactose, NF (anhydrous) and 322 g of tacrolimus (not dissolved) were passed through a Fitzmill and into container 1. Next, the solid dispersion portion of the formulation was passed through a Fitzmill and into container 1 as well. Following that, 1.800 kg of lactose, NF (anhydrous) was passed through a Fitzmill and collected in container 1. Then another 180 g of lactose, NF (anhydrous) was passed through a Fitzmill and added to container 1 as well.

The mixture of container 1 was then mixed in a ribbon mixer for 20 minutes. To this, 45.0 g of magnesium stearate, NF was added after passing thought a #40 mesh screen and mixed for an additional 5 minutes. This mixture was then passed through a roller compactor. The roller compacted mixture was then added to a ribbon mixer along with 45.0 g of magnesium stearate, NF which was passed through a #40 mesh screen. This mixture was then mixed for 5 minutes and discharged into a container for encapsulation into appropriate sized (no. 4) capsules.

As indicated earlier, pharmaceutical formulations produced according to the process of the present invention have been shown to be bioequivalent to FDA approved formulations. Specifically, a tacrolimus formulation comprising from 50-85% tacrolimus as a solid dispersion has been shown to be bioequivalent to the reference listed brand product as specified by the FDA Orange Book.

In accordance with the above, a bioequivalency study was conducted on healthy fasted subjects to determine the bioavailability of the test product with 100% dissolved tacrolimus in the solid dispersion versus PROGRAF Capsules, the Reference Listed Drug (RLD) per the Orange Book. The results indicate that the Cmax 90% Confidence Interval (CI), based on analysis of natural log-transformed data, was 136.94-162.37% and the $AUC_{0-T}$ 90% CI was 114.19-156.22%. The FDA recognized acceptance criteria for the CI for Cmax and AUC is 80-125%. Surprisingly this study demonstrates that by dissolving 100% of the drug substance in the solid dispersion a super-bioavailable product is formed.

Next, a bioequivalency study was conducted on healthy fasted subjects to demonstrate the effect of reducing the percentage of dissolved tacrolimus used to form the solid dispersion on bioavailability of the test product compared the RLD (reduced from 100% down to 80% and down to 50%). The results for 80% dissolved drug study showed a Cmax 90% CI of 109.03-131.81 and the $AUC_{0-T}$ 90% CI was 92.47-111.61%. The results of the 50% dissolved drug study showed a Cmax 90% CI of 72.86-88.37% and the $AUC_{0-T}$ 90% CI was 80.46-97.44%. The percent of dissolved drug in the solid dispersion was demonstrated to be critical with respect to bioequivalency of the test product versus the RLD.

A bioequivalency study was conducted on healthy fasted subjects to evaluate 65% dissolved tacrolimus used to form the solid dispersion on bioavailability of the test product compared to the RLD. The results showed a Cmax 90% CI of 94.43-106.75% and the $AUC_{0-T}$ 90% CI was 93.24-106.94%. The test product was bioequivalent to the RLD with 65% dissolved tacrolimus in the solid dispersion compared to the RLD which, to the best of our knowledge and without being bound to any particular theory, has 100% dissolved tacrolimus, or close thereto.

It will be apparent that one advantage of the present invention is that less processing of the active ingredient is required since only a portion of the macrolide requires conversion to an absorbable form, such as in the solid dispersion portion of the formulation of the invention. Additionally, use of a vacuum dryer along with surfactants, as shown in the prior art, is eliminated thereby reducing equipment and ingredients needed when producing the oral dosage formulation. Further, undesirable solvents used in the preparation of conventional formulations of tacrolimus, such as dichloromethane which is used to dissolve certain carriers, are eliminated. These advantages all result in less time and expense required on the part of the manufacturer, as well as elimination of certain undesirable chemicals, thus making the product more economical for the end users while remaining bioequivalent to the reference listed brand product as specified by the FDA Orange Book.

The invention has been described hereinabove using specific examples. However, it will be understood by those skilled in the art that various alternatives may be used and equivalents may be substituted for elements or steps described herein, without deviating from the scope of the invention. Modifications may be necessary to adapt the invention to a particular situation or to particular needs without departing from the scope of the invention. It is intended that the invention not be limited to the particular implementation described herein, but that the claims be given their broadest interpretation to cover all embodiments, literal or equivalent, covered thereby.

What is claimed is:
1. A pharmaceutical formulation comprising:
a. a solid dispersion of a macrolide compound of formula (I); and
b. a non-dispersed, non-dissolved, crystalline form of the macrolide compound;
wherein the amount of the solid dispersion of the macrolide compound is from about 50% to about 85% of the combined amount of the solid dispersion and the non-dispersed, non-dissolved crystalline form,
wherein the combined amount equals 100% of a pharmaceutically acceptable amount,
wherein the compound of formula (I) is represented by the following:

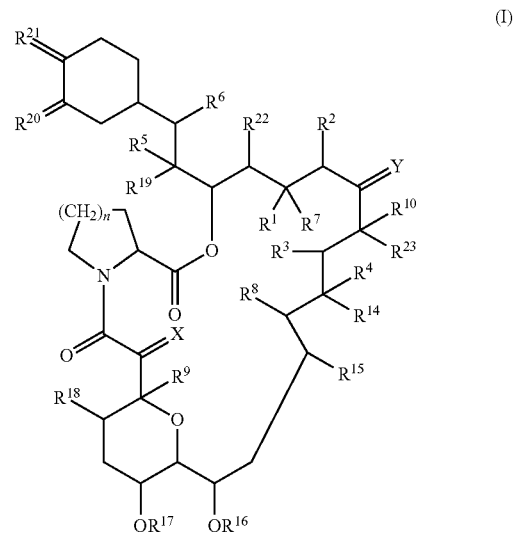

(I)

wherein each vicinal pair of $R^1$ and $R^2$, $R^3$ and $R^4$, $R^5$ and $R^6$ independently may,
a) represent two vicinal hydrogen atoms, or
b) form a second bond between the vicinal carbon atoms to which they are attached;
in addition to the meanings above, $R^2$ may represent an alkyl group;
$R^7$ represents hydrogen, hydroxy group, protected hydroxy or alkyloxy group or, in conjunction with $R^1$, it may represent oxo group;
$R^8$ and $R^9$ independently represent hydrogen or hydroxy group; $R^{10}$ represents hydrogen, alkyl group, alkyl group substituted by one or more hydroxy groups, alkenyl group, alkenyl group substituted by one or more hydroxy groups, or alkyl group substituted by oxo group;
X represents oxo group, (hydrogen atom, hydroxy group), (hydrogen atom, hydrogen atom) or —$CH_2O$—;
Y represents oxo group, (hydrogen atom, hydroxy group), (hydrogen atom, hydrogen atom) or N—$NR^{11}$ $R^{12}$ or N—$OR^{13}$;
$R^{11}$ and $R^{12}$ independently represent hydrogen atom, or alkyl, aryl or tosyl group;
$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;

$R^{20}$ and $R^{21}$ independently represent oxo group, or they may independently represent ($R^{20}_a$, hydrogen atom) and ($R^{21}_a$, hydrogen atom) respectively; $R^{20}_a$ and $R^{21}_a$ independently represent hydroxy group, alkyloxy group, or $OCH_2OCH_2CH_2OCH_3$ or $R^{21}_a$ is protected hydroxy group;

in addition $R^{20}_a$ and $R^{21}_a$ may together represent an oxygen atom in an epoxide ring;

n is 1, 2 or 3;

in addition to the meanings above, Y, $R^{10}$ and $R^{23}$, together with the carbon atoms to which they are attached, may represent a 5- or 6-membered N- , S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —$CH_2Se(C_6H_5)$.

2. The formulation of claim 1 wherein the macrolide compound is 17-allyl-1,14-dihydroxy-12-[2-(4-hydroxy-3-methoxy-cyclohexyl)-1-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone(tacrolimus).

3. The formulation of claim 2 wherein the amount of the solid dispersion of tacrolimus is from about 55% to about 75% of the combined amount of the solid dispersion and the non-dispersed, non-dissolved crystalline form.

4. The formulation of claim 2 wherein the amount of the solid dispersion of tacrolimus is about 65% of the combined amount of the solid dispersion and the non-dispersed, non-dissolved crystalline form.

5. The formulation of claim 1 wherein said solid dispersion of the macrolide compound comprises the macrolide compound and a solid carrier, wherein the macrolide compound is dispersed onto the solid carrier, wherein the water solubility of the macrolide compound is enhanced.

6. The formulation of claim 5 wherein the macrolide compound is tacrolimus.

7. The formulation of claim 5 wherein the solid carrier is hydroxypropylmethyl cellulose (HPMC).

8. The formulation of claim 6 wherein the solid carrier is hydroxypropylmethyl cellulose (HPMC).

9. The formulation of claim 8 wherein the amount of the solid dispersion of tacrolimus is from about 55% to about 75% of the combined amount of the solid dispersion and the non-dispersed, non-dissolved crystalline form.

10. The formulation of claim 9 wherein the amount of the solid dispersion of tacrolimus is about 65% of the combined amount of the solid dispersion and the non-dispersed, non-dissolved crystalline form.

11. The formulation of claim 1 comprising an oral dosage form.

12. The formulation of claim 1 wherein the $C_{max}$ at 90% confidence interval (CI) is at least 72.86-88.37% and the $AUC_{0-T}$ at 90% CI is at least 80.46-97.44% with regard to the reference listed drug in the FDA Orange Book.

13. The formulation of claim 1 wherein said solid dispersion is formed by dissolving the macrolide compound in a solvent, mixing the dissolved macrolide compound with a carrier and drying the macrolide compound on said carrier which removes said solvent.

14. The formulation of claim 11 wherein the oral dosage form is a capsule and the pharmaceutically acceptable amount is selected from 5.0 mg, 1.0 mg and 0.5 mg.

15. The formulation of claim 14 wherein the macrolide compound is tacrolimus.

* * * * *